(12) United States Patent
Evrard et al.

(10) Patent No.: US 6,652,523 B1
(45) Date of Patent: Nov. 25, 2003

(54) MONOLATERAL ORTHOPEDIC DEVICE WITH EXTERNAL FIXING FOR IMMOBILIZING A FRACTURED BONE

(75) Inventors: Patrick Evrard, Orleans (FR); Michel Di Shino, 163, rue des Roissis, 92140 Clamart (FR); Christian Steenman, Residence "Le Lys", 79, Avenue de Paris, 78000 Versailles (FR); Georges Dalzotto, 64, , rue de l'Egalite, 92 Issy-les-Moulineaux (FR); Sylvain Rigal, 75, rue Paul Pade, 92140 Clamart (FR)

(73) Assignees: Delegation General pour l'Armement, Armees (FR); Michel Di Shino, Clamart (FR); Sylvain Rigal, Clamart (FR); Christian Steenman, Paris (FR); Georges Dalzotto, Issy-les-Moulineaux (FR)

( * ) Notice: Subject to any disclaimer, the term of this patent is extended or adjusted under 35 U.S.C. 154(b) by 0 days.

(21) Appl. No.: 09/582,430

(22) PCT Filed: Dec. 16, 1999

(86) PCT No.: PCT/FR99/03158

§ 371 (c)(1),
(2), (4) Date: Nov. 3, 2000

(87) PCT Pub. No.: WO00/38585

PCT Pub. Date: Jul. 6, 2000

(30) Foreign Application Priority Data

Dec. 29, 1998 (FR) .............................. 98 16524

(51) Int. Cl.⁷ .................................. A61F 5/04
(52) U.S. Cl. .............. 606/54; 606/56; 606/59
(58) Field of Search .............................. 606/54, 57, 59, 606/58

(56) References Cited

U.S. PATENT DOCUMENTS

| 4,483,334 A | * 11/1984 | Murray ....................... 403/391 |
| 4,620,533 A | 11/1986 | Mears |
| 4,662,365 A | 5/1987 | Gotzen et al. |
| 5,624,440 A | 4/1997 | Huebner |
| 5,741,252 A | 4/1998 | Mazzio et al. |
| 5,752,954 A | * 5/1998 | Mata et al. ................... 606/53 |
| 6,409,729 B1 | * 6/2002 | Martinelli et al. ............ 606/59 |

FOREIGN PATENT DOCUMENTS

| DE | 3539616 A1 | 5/1986 |
| DE | 9103480 U1 | 7/1991 |
| DE | 29512917 U1 | 11/1995 |
| FR | 2457676 | 6/1979 |
| FR | 2442044 | 6/1980 |
| FR | 2551650 | 3/1985 |
| FR | 2553994 | 5/1985 |
| FR | 2688685 | 9/1993 |

\* cited by examiner

Primary Examiner—Cary E. O'Connor
Assistant Examiner—Candice C. Melson
(74) Attorney, Agent, or Firm—Oliff & Berridge, PLC

(57) ABSTRACT

The invention applies to the field of medicine, particularly to bone surgery. The invention relates to a monolateral orthopedic external fixation device for immobilizing a fractured bone having a rigid support, at least two pins screwed into the bone and joined to the rigid support by a connecting mechanism comprising a pin-holding device composed of two identical parts forming a clamp whose two opposing faces have depressions. These depressions are able to receive and hold pins with diameters from 3 to 6 mm.

10 Claims, 6 Drawing Sheets

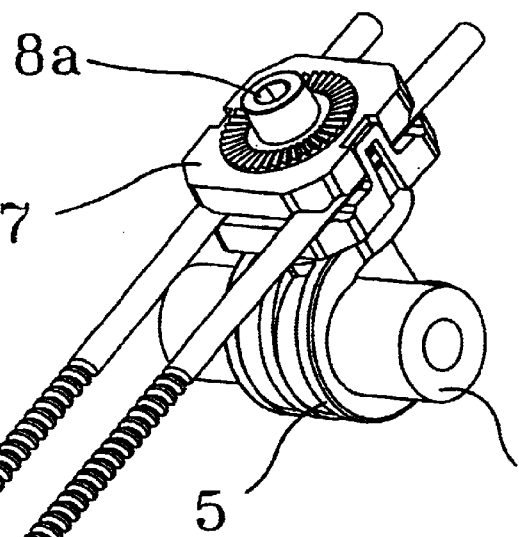
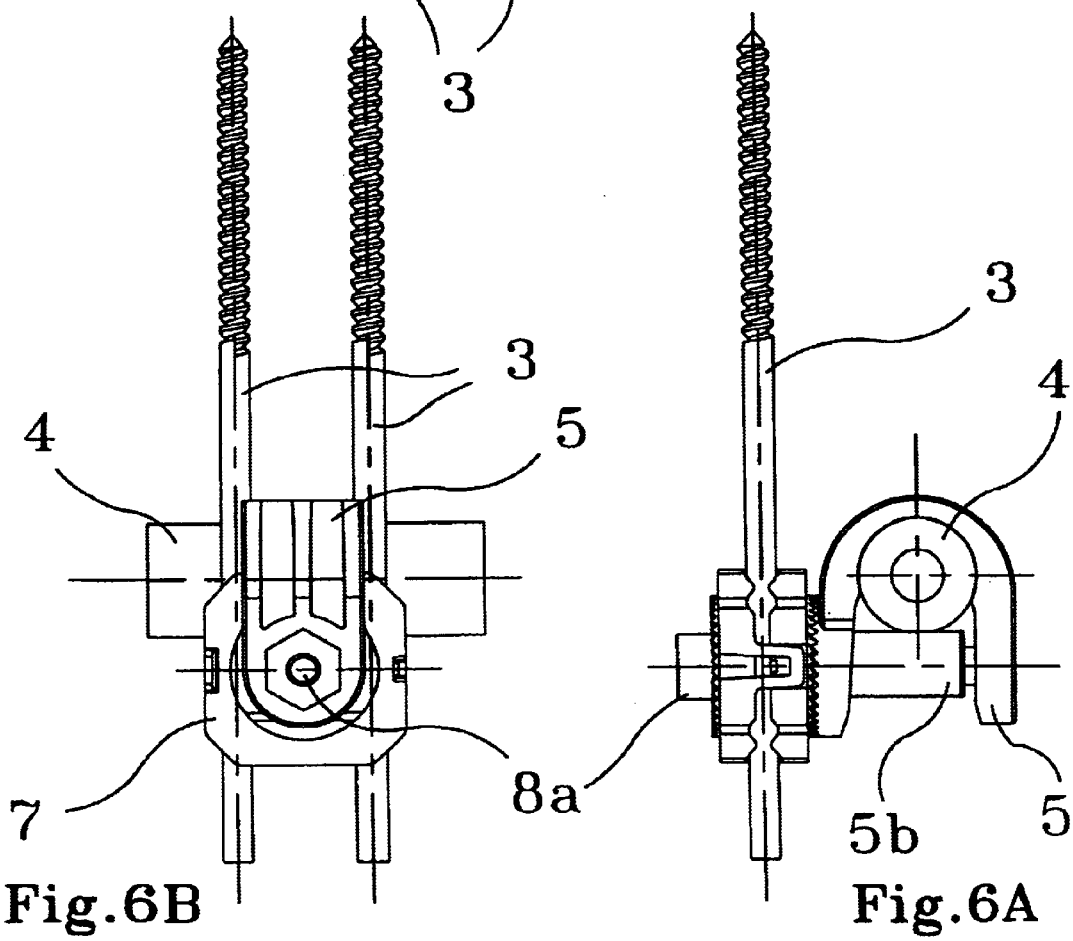
Fig.6
Fig.6B　　Fig.6A

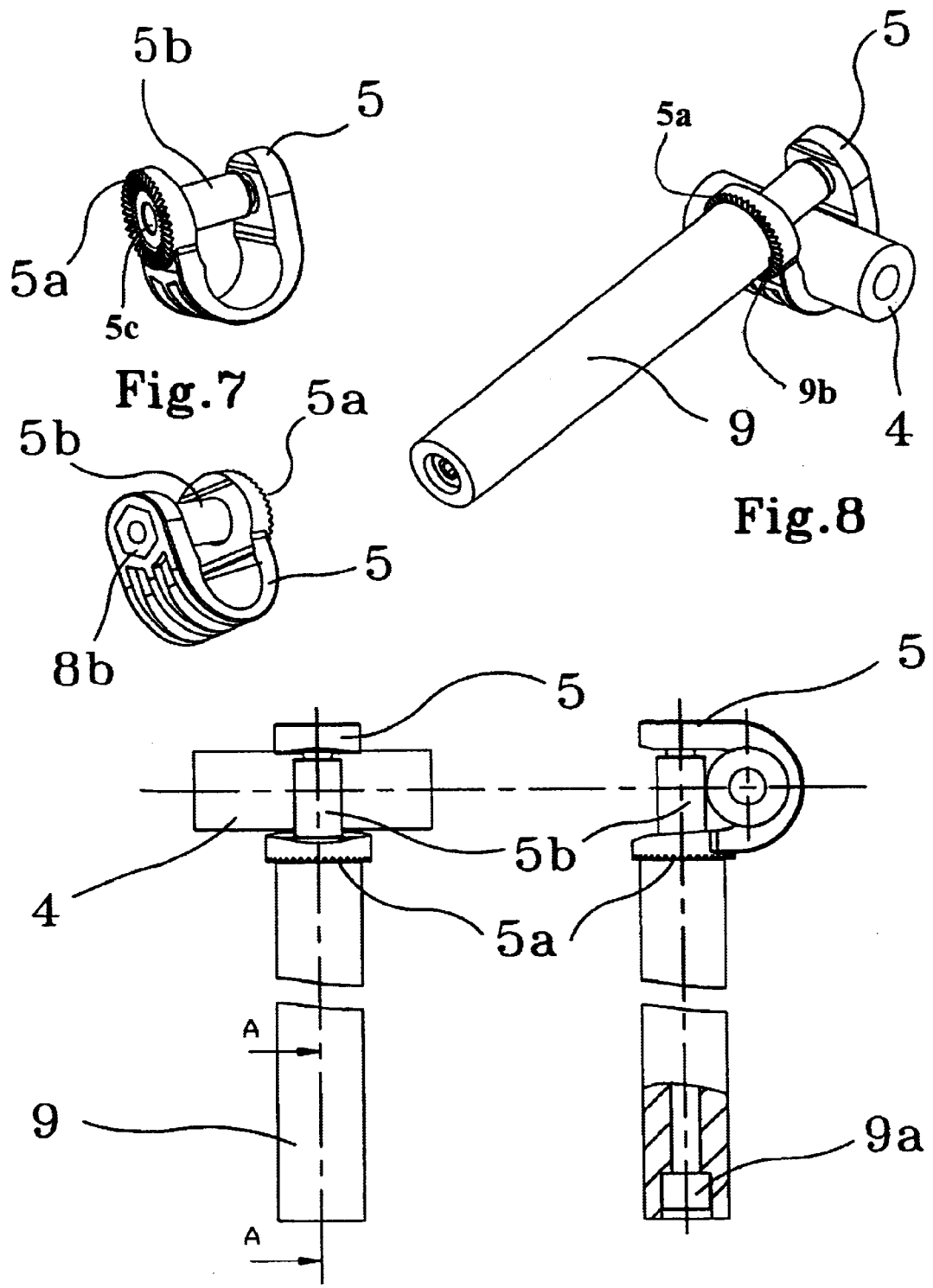

MONOLATERAL ORTHOPEDIC DEVICE WITH EXTERNAL FIXING FOR IMMOBILIZING A FRACTURED BONE

BACKGROUND OF THE INVENTION

1. Field of the Invention

The technical area of the present invention is that of external orthopedic devices designed to immobilize fractured limbs and reduce fractures. These types of devices are used for osteosynthesis with an external fixation device.

Treatment of fractures that are open, dirty, have large openings, are old, or caused by projectiles with high kinetic energies require external fixation. The fixation of a fracture, particularly an open fracture, must be stable, because compression, traction, twisting, and flexing stresses at the site of the fracture are transmitted to the external fixation device through the bone-pin connection. Rigidity of the fixation device is hence of the utmost importance in consolidating the bone fragments of a fracture. There are numerous external fixation devices of different types—unilateral, frame, or circular—on the market.

The majority of operations with fixation devices performed on an emergency basis, particularly by field surgery under wartime or disaster conditions, usually have to be repeated because of reduction defects. Perfect initial surgery is rare.

There are only two options for the subsequent procedure:

remove the pins, re-perform the reduction, and reinsert the pins through a new connecting bar, thereby losing the value of the initial fixation;

leave the pins in place, and reduce by changing the assembly with two short bars (upper and lower) joined by a connecting means, whereby the assembly loses its initial rigidity.

2. Description of Related Art

External fixation devices composed of rigid tubes or equivalent means in which the pins engage and are held by screws are described for example in patents FR 2,442,044, FR 2,551,650, and FR 2,553,994.

In particular, Patent 2,457,656 describes a unilateral type fixation device for reducing a fracture comprising a main tube supporting two tube segments joined to the first with spherical mounts. Collars allow the two segments to slide relative to the main tube, and each tube has, in two mutually perpendicular planes, diametrically opposite, regularly spaced, threaded holes to receive the pins and the locking screws.

These fixation devices, worn by ambulant patients, have numerous drawbacks.

For instance, insertion on an emergency basis requires reduction and provisional containment of the bone site, or at least correct alignment of the limb if bone substance has been lost, before the pins are inserted. This constraint is the reason for many imperfect initial insertions.

In addition, the spacing of the pins is strictly defined by the holes in the tubes wherein the pins are located in a single plane and parallel to each other. This prevents flexibility in orienting or spacing the pins implanted in the bone.

Further, an apparatus having a large number of component parts, each having different diameters, develops to include a main tube, a tube segment, a spherical mount, a collar, and a pin. The large number of parts makes assembly difficult and is time-consuming when the surgeon is unaccustomed to their use.

Moreover, the various basic parts are not radiotransparent and are heavy because they are made of metal. The latter point is a drawback not only for the patient but also for field surgical teams carrying instrument kits.

U.S. Pat. No. 4,483,334 describes an external fixation device for fractures having pins screwed into the bone on either side of the fracture, a pair of rods connected to these pins on either side of the fracture, and a bridge connecting the rods with each other. The connecting mechanisms connecting each pin to the rods consist of a one-piece U-shaped assembly clamped to the pins, and a collar that is adapted to the diameter of the rods. The pins, rod, pin assemblies, and collars are held together by a single screw ensuring holding in all directions.

German Utility Model DE 91 03 480 describes a device for immobilizing a finger or a hand in the event of a fracture consisting of spikes screwed on either side of the fracture that are held together by a connecting rod. The connecting mechanism between the spikes and the connecting rod is comprised of a U-shaped collar, a socket, a screw provided with a hole for the spike to pass through, and a nut. When the nut is tightened, the spike is locked.

These two devices enable only one pin to be fixed by a connecting mechanism.

German Patent DE 295 12 917 describes an orthopedic device having a pin assembly for simultaneously holding at least two pins in parallel.

This assembly is composed of two identical parts forming a clamp. The clamp has depressions on two opposing faces for gripping and holding the pins.

This assembly has the drawback of holding only one pin diameter. In other words there is one type of assembly for each pin diameter. Thus, assemblies of different configurations must be available in order to achieve the immobilization desired.

Other orthopedic options are available that are lighter than the foregoing, and are made of radiotransparent and non-magnetic materials. An example of such is the fixation device described in French Patent FR 2,688,685. This device has a solid, rigid rod having transverse orifices for passage of pins screwed into the bone. These pins are fastened to the rod by fixation inserts or tightening collars. However, the spacing of the orifices, and hence the spacing of the pins, is strictly defined and invariable.

SUMMARY OF THE INVENTION

One goal of the present invention is to provide an external orthopedic fixation device compatible with existing fixation devices, particularly those used by the member countries of the North Atlantic Treaty Organization (NATO), for precise reduction of fractures by precise adjustments with several degrees of freedom.

Another goal of the present invention is to provide an orthopedic device that simplifies the installation of material by a non-specialist surgeon, thereby offering the opportunity to correct axial defects without modifying the pins in place, or requiring additional epiphyseal holding devices.

The further goal of the present invention is to provide an external fixation device having good rigidity and simultaneously:

simplifying the repositioning of axial defects without modifying the pins in place;

providing compatibility with the pins of employed with various fixation devices already in use, such as those employed in NATO countries;

enabling the use of the device by a non-specialist because the number of component parts is very small;

causing the reduction of fractures with the fixation device in place;

allowing muscle flaps to be created to cover the limbs involved by using a single-plane or at least unilateral assembly;

exploring an extremely simple design of the epiphyseal holding devices;

using self-drilling and self-tapping pins of different diameters for adaptation the various types of surgery;

more easily monitoring bone consolidation by x-ray or magnetic resonance imaging due to total radiotransparency of the device;

adding comfort to the patient because the implants are light.

For this purpose, the monolateral orthopedic device with external fixing for immobilizing a fractured bone has, in known fashion, a rigid support disposed parallel to the bone, at least two pins screwed into the bone and joined to the rigid support by a connecting mechanism comprising a pin-holding device composed of two identical parts forming a clamp whose two opposite faces have depressions. This device is characterized in that the depressions are able to receive and hold pins with diameters from 3 to 6 mm.

Preferably, the depressions of the device have different directions, i.e., the depressions in one of the directions enable pins 3 or 4 mm in diameter and parallel with each other to be held, and the depressions in the other direction, perpendicular to the previous direction, enable pins 5 or 6 mm in diameter and parallel with each other to be held.

Preferably, the connecting mechanism comprises a collar that can slide around the support and a single removable screw providing omnidirectional locking of each connecting mechanism and each pin relative to the support and its corresponding pin-holding device.

The pin-holding device can have a foolproofing mechanism, whereby the two identical clamp-forming parts each have a peg and a tongue accommodated in an orifice and a notch respectively of the other identical part. This mechanism makes it possible to guide one of the two parts relative to the other without hesitation.

Preferably, the device has means of assembling the pin-holding devices to the collars. These means can be crenellated surfaces made in each face to contact with the pin-holding devices and with each collar. This ensures precise indexing, cohesion of the parts with each other, and full immobilization of the pins relative to the rigid support.

Preferably, the collars, made of a flexible material, are clipped onto the rigid support and the transverse support. They may have a spacer to maintain a constant distance between the two ends of the collar and limit the torque of the screw.

Preferably, the rigid support is comprised of a cylindrical tube made of carbon.

Preferably, the entire device, with the exception of the pins, is made of a radiotransparent, non-magnetic material.

According to one embodiment, the device can have a transverse support joined to a rigid support by a collar to hold an epiphysis of the fractured bone using at least one pin screwed into the epiphysis and a connecting mechanism mounted on the transverse support.

The various types of parts in the device can have different colors to facilitate their identification when the device is mounted on the patient.

This device has the advantage of having a very small number of parts. The minimizing of parts saves a great deal of time and facilitates assembly of the device, both of which are essential in emergency surgery by an inexperienced surgeon.

Another advantage is that the support/collar and collar/pin-holding device connections allow the pins to move in all directions so that the device can be adapted when correcting alignment defects without modifying pins already in place.

Because the material is a light weight carbeon-type synthetic material, the consolidation x-rays are easy to read and the device is easy for the surgeon or patient to carry.

Another advantage is that the two types of pin-holding devices are fully compatible with the various pins already used this type of operation.

Other characteristics and advantages of the invention will emerge from the detailed nonlimiting description provided below.

The description below refers to the attached drawings that represent, without being limiting in nature, one embodiment of an orthopedic device with external fixing according to the present invention.

BRIEF DESCRIPTION OF THE DRAWINGS

FIG. 6 is a view according to FIG. 3 of the mounting of two pins on a rigid support with the aid of a clamp-shaped pin-holding device.

FIGS. 6A and 6B show the mounting arrangement of FIG. 6 in cross section.

FIG. 7 shows two elevations of a collar according to the invention.

FIG. 8 is a partial elevation view of the epiphyseal mounting arrangement shown in FIG. 2.

FIG. 8A is the mounting arrangement of FIG. 8 in a top view.

FIG. 8B is a partial cross-sectional view along line AA in FIG. 8A.

The attached figures show a monolateral orthopedic device with external fixing used for temporary immobilization of a fractured bone 2.

DETAILED DESCRIPTION OF PREFERRED EMBODIMENTS

Figure 1:
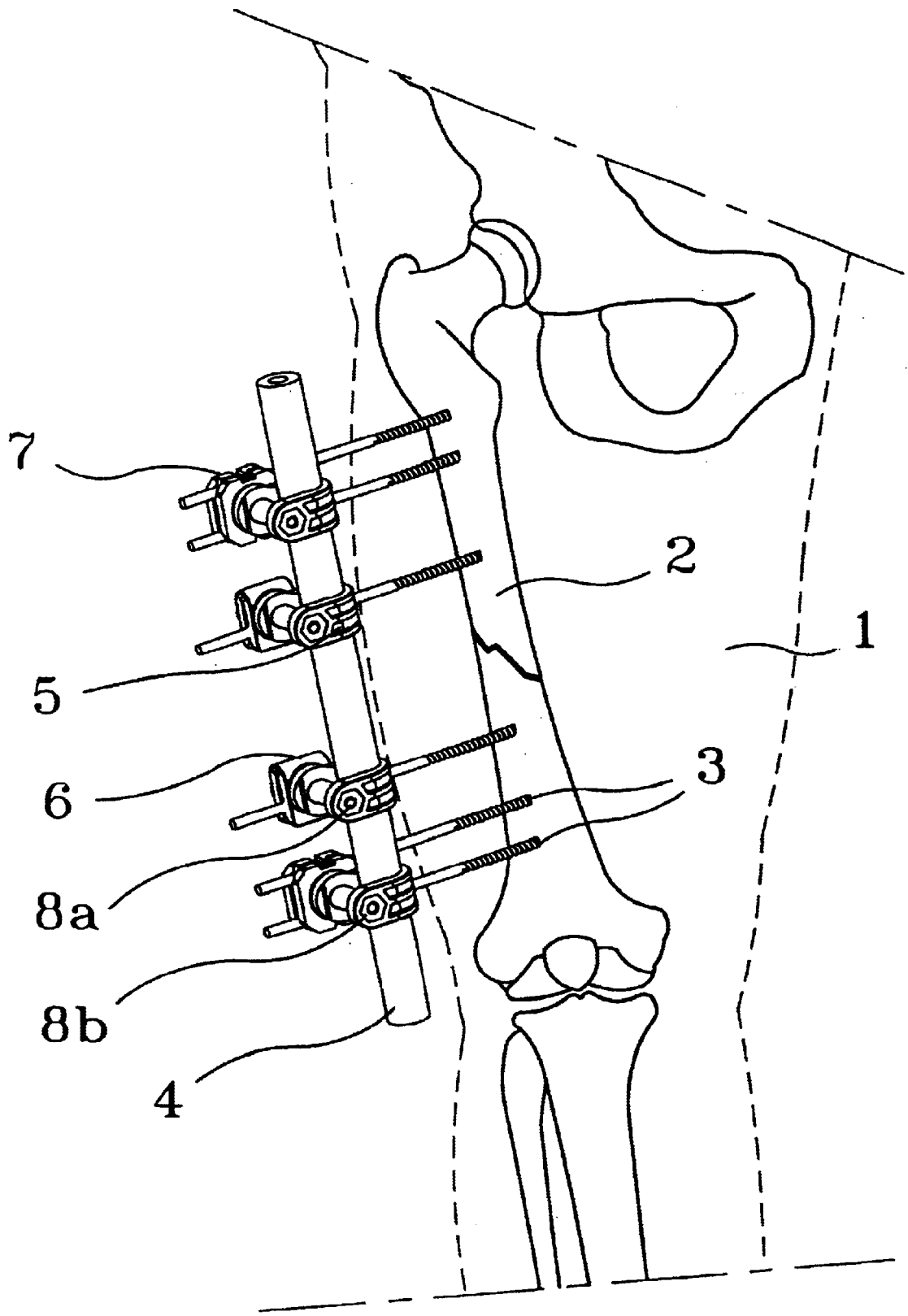
FIG. 1 is a perspective view of an external fixation device in its utilization condition, for example for immobilizing a fracture in a long bone of the femur type.
Figure 2:
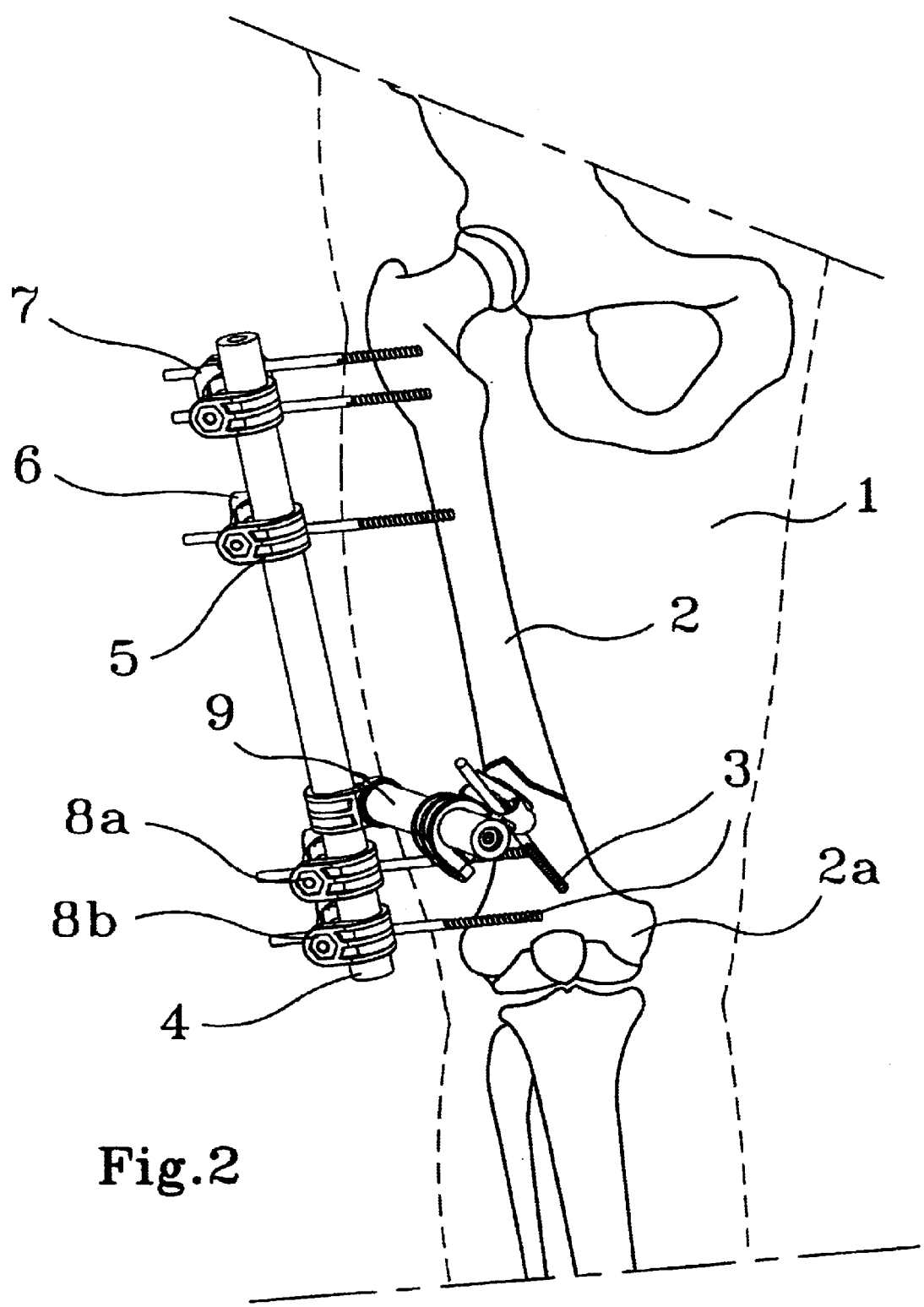
FIG. 2 is a view of the device according to FIG. 1, showing the mounting of a epiphyseal holding device.

As an example, FIGS. 1 and 2 show a device according to the invention disposed in parallel on a fractured femur 2 of a thigh 1 of an injured patient. The device is placed along and outside thigh 1. Femur 2 is shown after reduction of the fracture.

The device has at least two pins 3 screwed into bone 2 on either side of the fracture and joined to a rigid support 4 by a connecting mechanism.

Pins 3 of a known type, made of a stainless-type metal, are preferably provided with a self-tapping end and can be 3 to 6 mm in diameter.

Rigid support 4 is comprised of a smooth cylindrical tube made in known fashion by winding carbon fibers.

The connecting mechanism is a combination of a pin-holding device 6 or 7 with a collar 5, using a single fixation means screw 8a.

Collars 5, made of a flexible synthetic material, are clipped onto rigid support 4 and can slide around and along it. These collars 5, adapted to the diameter of the rigid support and U-shaped, are perforated at each end (FIG. 7). A crenellated ring 5a is formed in the outer part of one of the ends and a removable spacer 5b, made of a hollow cylindrical tube, is disposed between the two ends of the collars to keep them at a constant distance from each other. The outer part of the orifice provided in this crenellated ring end has a circular opening 5c to facilitate the relative positioning of each collar relative to pin-holding devices 6 or 7. An insert 8b is lodged in the orifice of the other end of the collar and sunk in the thickness of this end. This insert is provided with a threaded orifice.

The bodies of both types of pin-holding devices, 6 and 7, are pierced transversely.

Fixation means screw 8a is a threaded screw of known type long enough to pass through the transverse opening of the pin-holding device, spacer 5b, and the ends of the corresponding collar 5. The fixation means end of the screw 8a engages the threaded orifice of insert 8b to ensure locking of the connecting mechanism and the corresponding pins 3 in all directions, once the screw has been tightened.

The length of spacer 5b is adjusted to limit the tightening torque of fixation means screw 8a, while completely immobilizing collar 5 relative to rigid support 4 once screw 8a has been locked.

The device has two different types of pin-holding devices 6 and 7.

Figures 3, 4:
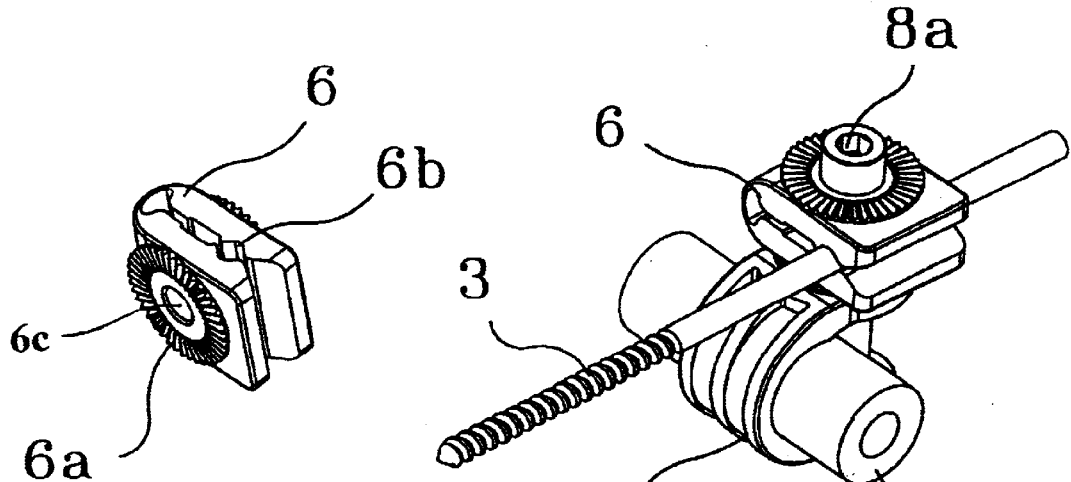
FIG. 3 is a partial perspective view of the mounting of the pin-joining means on a rigid support of the device, with a one-piece pin-holding device.
FIG. 4 shows a one-piece pin-holding device in elevation.
Figures 3A, 3B:
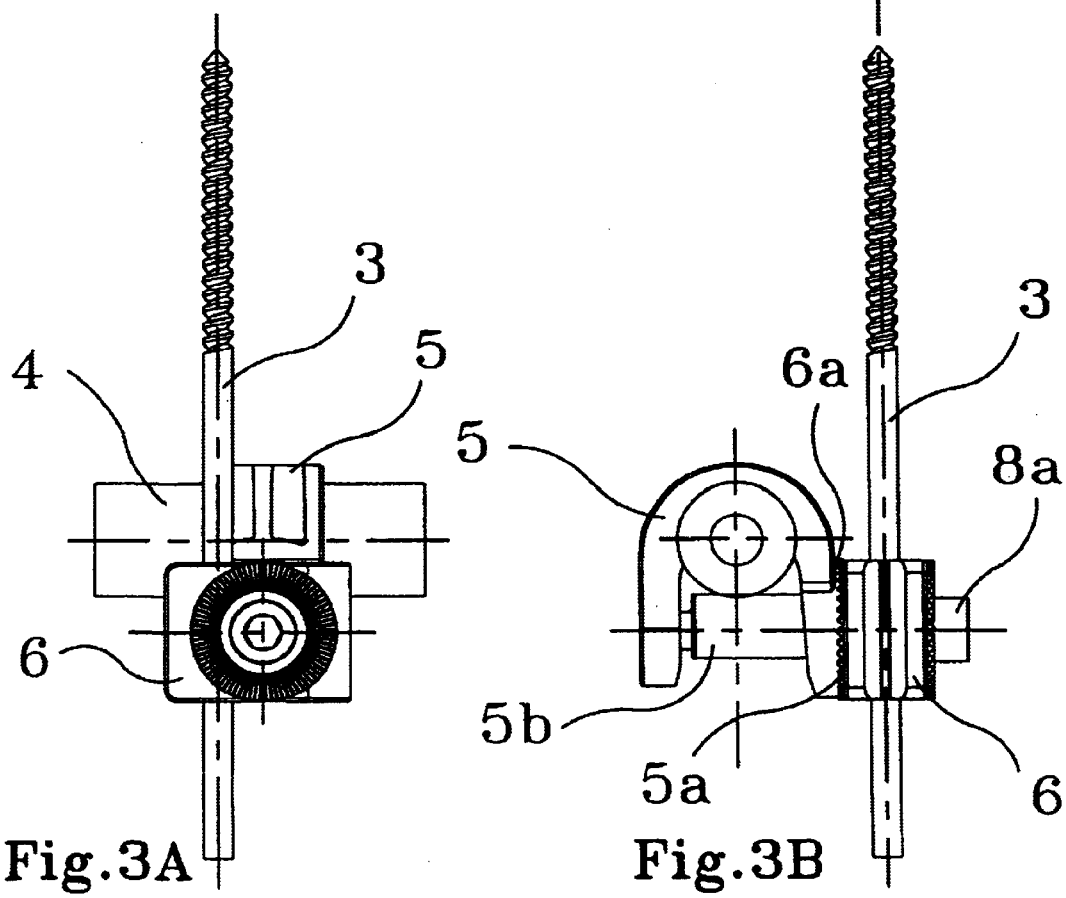
FIGS. 3A and 3B show the arrangement in FIG. 3 in cross section.

Pin-holder 6, FIG. 4, is made of a one-piece U-shaped part comprising two symmetrical rectangular sides connected to each other by a curved, elastic element so that the end of at least one pin 3 can be clipped between the two rectangular elements. The sides of pin-holder 6 have an internal bevel to facilitate insertion of the ends of pins 3.

Figure 5:
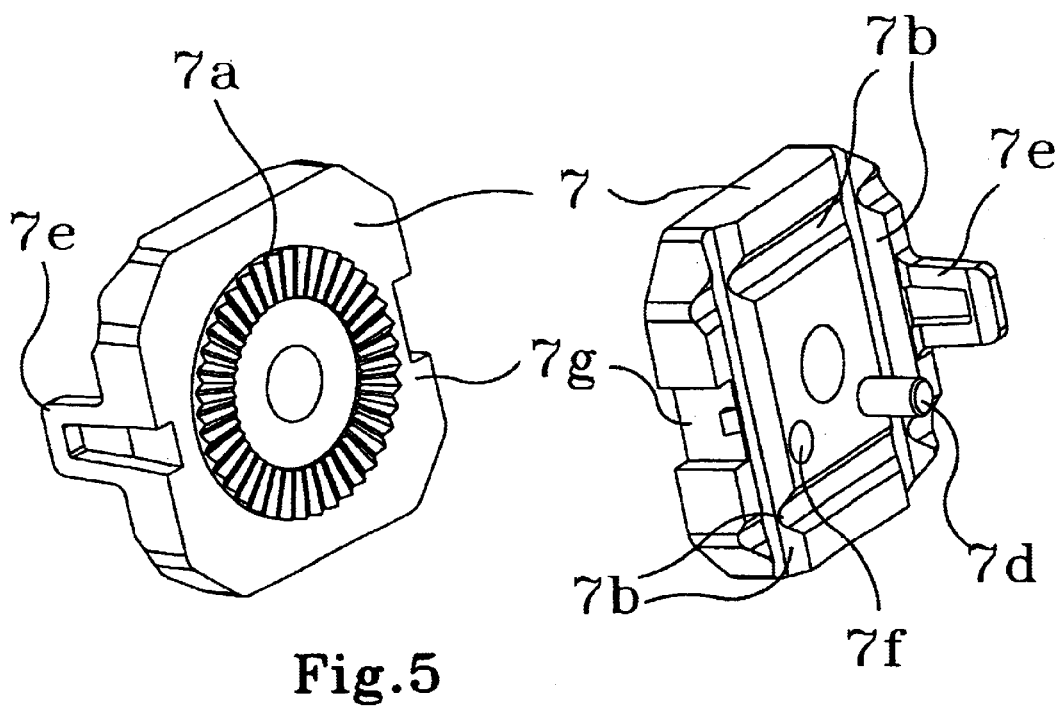
FIG. 5 is an elevation view of a clamp-shaped pin-holding device according to the invention, showing its two identical parts dissociated with their outer and inner faces.
Figures 5A, 5B:
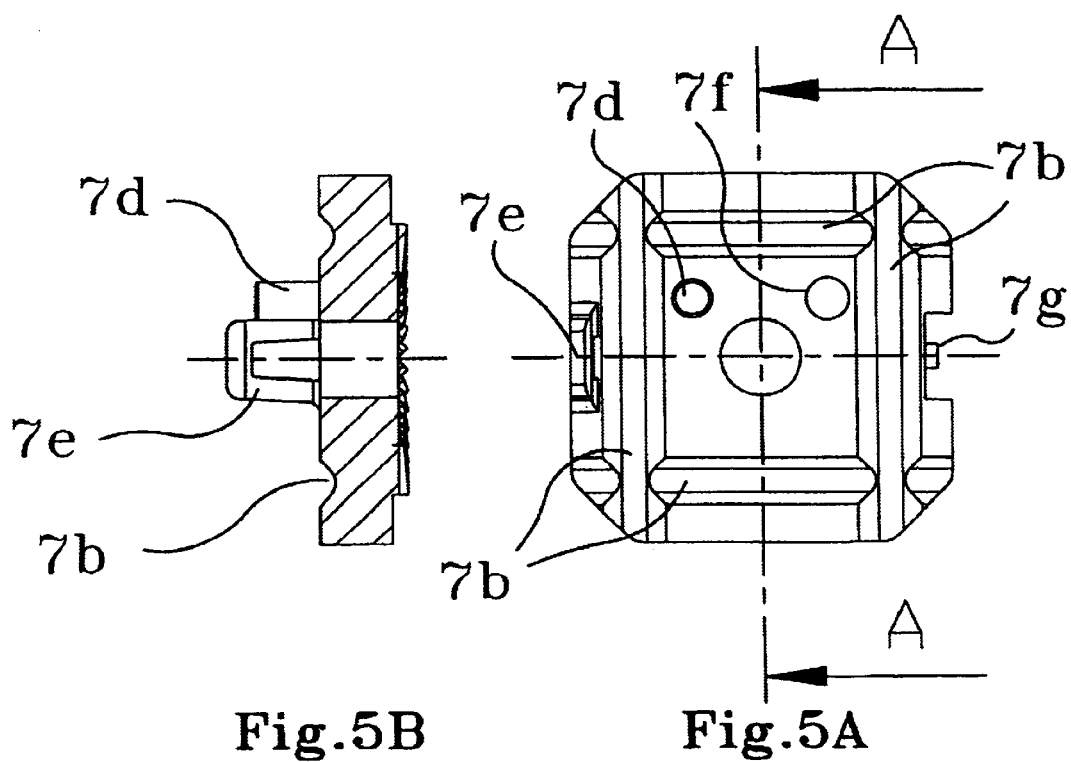
FIG. 5A is a plan view of the internal face of one of the identical parts of FIG. 5.
FIG. 5B is a cross-sectional view along line AA in FIG. 5B.

Clamp-shaped pin-holder 7 FIGS. 5 to 5B, has two rectangular dissolvable parts having a peg 7d projecting on their inner faces, an eccentric transverse orifice 7f, a notch 7g in one of the sides, and a flexible tongue 7e attached to the opposite side.

When the two dissolvable parts are assembled, peg 7d and tongue 7e of one of the parts are accommodated in orifice 7f and notch 7g respectively of the other part to form a clamp in which the ends of the two pins 3 are placed. If necessary, this pin-holding device 7 is suitable for receiving the end of a single pin 3.

The outer faces of the two pin-holding device types 6 and 7 have a crenellated ring 6a and 7a identical to the ring 5a of collars 5. Crenellated ring 5a of the collar is placed in contact with crenellated ring 6a or 7a of the pin-holding device 6 or 7 used, to ensure precise indexing and optimize their cohesion and immobilization relative to rigid support 4.

Depressions 6b and 7b are provided in the thickness of the inner faces of the two pin-holders 6, 7 and each receives the end of a pin 3. These depressions 6b, 7b are in the shape of a recess with a triangular section, FIGS. 4, 5B, over the entire length or width of pin-holding devices 6 and 7. The particular shapes of these depressions prevent any possibility of the cylindrical end of the pin rotating inside device 6 or 7.

When bone 2 is fractured at epiphysis 2a, FIG. 2, pins 3 have to be placed in this epiphysis to ensure correct immobilization of the fractured bone.

For this purpose, the device has a transverse support 9 joined to rigid support 4 by a collar 5 similar to that described above.

This transverse support 9 is made of a small cylindrical tube made of carbon of the same type as rigid support 4. It is pierced along its lengthwise axis for insertion through one of its ends of a threaded screw 9a, FIG. 8B, or any other equivalent means, and screwed to insert 8b of a collar 5 to fasten it to rigid support 4 once screw 9a has been tightened.

This screw is similar to the screw 8a described above, but is longer so that it can adapt to the length of transverse support 9 and the spacing of the ends of collar 5. A crenellated ring 9b positioned on crenellated ring 5a of collar 5 is provided on the section of the other end of transverse support 9 to improve the fixation of this support to the collar while preventing any rotational movement of transverse support 9. One or more connecting mechanisms are mounted on this support 9, which has the same diameter as rigid support 4, as described above.

Except for pins 3, the entire device is made of a radiotransparent, non-magnetic material of the carbon type. This highly rigid material is also highly resistant to a repeated temperature of 140° and to the products used for sterilizing the device as a whole. To facilitate application of the device to the patient, the various types of parts used are in different colors.

The monolateral orthopedic device with external fixing operates as follows.

Once the fracture in bone 2 has been reduced and at least two pins 3 have been inserted on either side of the fracture, the surgeon mounts a connecting mechanism on the end of each pin. The connecting mechanism comprises at least a collar 5, pin holder 6, 7, pins 3, a fixation means screw 8a, insert 8b and rigid support 4.

A pin 3 end is clipped to a one-piece pin-holder device 6 and positioned in depression 6b. A collar 5 is placed on rigid support 4 and a spacer 5b is disposed between the ends of collar 5. Collar 5 and pin-holder device 6 are joined by placing crenellated rings 5a and 6a in contact. Thus, the orifices 6c, 5c of the pin-holder and collar respectively, and the spacer 5b are aligned for subsequent introduction of fixation means screw 8a, and the mechanism is locked by tightening it with a wrench until spacer 5b abuts the ends of the collar 5.

To join two neighboring pins 3 with rigid support 4, one side of a clamp-shaped pin-holder 7 is placed on the ends of the two pins 3, then the other side of pin-holder 7 is placed on the previous side by joining the peg 7d and tongue 7e of one side with orifice 7f and notch 7g of the other, respectively. At the same time, the ends of pins 3 are positioned in depressions 7b.

Assembly of this pin-holding device 7 with a collar 5 and rigid support 4 remains identical to the assembly described above.

Before fixation means screw 8a is tightened all the way, the angular arrangement of each connecting mechanism relative to pins 3 and rigid support 4 is precisely adjusted by modifying the relative positions of crenellated rings 6a, 7a, and 5a and moving collars 5 on rigid support 4 rotationally and translationally.

For the epiphyseal mounting arrangement, a transverse support 9 is joined to rigid support 4 by a collar 5 provided with a spacer 5b, the collar having previously been placed on the rigid support 4.

The crenellated ring 9b formed on the section of the end of transverse support 9 is positioned on ring 5a of the collar, then screw 9a is tightened until spacer 5b abuts the ends of the collar 5.

The connecting mechanisms are mounted on transverse support 9 in the same way as described for rigid support 4.

Preferably, screw 9a is held inside transverse support 9.

This device has a very small number of parts and is extremely simple to mount, making it fully suitable for emergency operations conducted under particularly arduous conditions.

The orthopedic device with external fixing for immobilizing a fractured bone has just been described, solely as a nonlimiting example. Of course, a number of modifications to the above example can be made by one skilled in the art without departing from the scope of protection defined by the attached claims.

What is claimed is:

1. A monolateral device with external fixing for immobilizing a fractured bone comprising:
   a rigid support;
   at least two pins screwable into the bone and joined to the rigid support by a connecting mechanism comprising
      a pin-holding device composed of two parts forming a clamp whose two opposing faces have depressions extending different directions, the depressions in one of the directions enabling pins 3 or 4 mm in diameter and parallel with each other to be held, and the depressions in the other direction, perpendicular to the previous direction, enabling pins 5 or 6 mm in diameter and parallel with each other to be held;
      a collar that can releasably translate and rotate about the rigid support; and
      a single removable screw,
   wherein the collar and the pin-holding device have crenellated surfaces made to contact one another to ensure precise indexing of the pin-holding device relative to the collar about a rotational axis of the collar, cohesion of the elements with each other, and full immobilization of the pins relative to the rigid support, and the single removable screw provides omnidirectional locking of each connecting mechanism and each pin relative to the rigid support and its corresponding pin-holding device.

2. The device according to claim 1, wherein the collar has a spacer to maintain a constant distance between two ends of the collar and limit the torque of the single removable screw.

3. The device according to claim 1, further comprising a second connecting mechanism include a second pin-holding device comprising a one-piece, U-shaped part having an internal bevel to receive one of the pins, a second collar that can slide around the rigid support, and a second single removable screw,
   wherein the second collar and the second pin-holding device have crenellated surfaces made to contact one another to ensure precise indexing of the second pin-holding device relative to the second collar about a rotational axis of the second collar, cohesion of the elements with each other, and full immobilization of the pins relative to the rigid support, and the second single removable screw provides omnidirectional locking of the second connecting mechanism and each pin relative to the rigid support and its corresponding pin-holding device.

4. The device according to claim 1, wherein the pin-holding device has a foolproofing mechanism guiding the positioning of one clamp-forming part relative to the other.

5. The device according to claim 4, wherein the foolproofing mechanism includes, on each of its clamp-forming parts, a peg and a tongue accommodated in an orifice and a notch respectively mated with the opposing side of the clamp.

6. The device according to claim 4, wherein the collar has a spacer to maintain a constant distance between two ends of the collar and limit the torque of the removable screw.

7. The device according to claim 1, wherein the rigid support is comprised of a cylindrical tube made of carbon.

8. The device according to claim 7, wherein the entire device, with the exception of the pins, is made of a radiotransparent, nonmagnetic, material.

9. The device according to claim 8, further comprising a transverse support joined to the rigid support by another collar to hold an epiphysis of fractured bone using at least one pin screwed into the epiphysis and a connecting mechanism mounted on the transverse support.

10. A monolateral device with external fixing for immobilizing a fractured bone comprising:
    a rigid support;
    at least two pins screwable into the bone and joined to the rigid support by a connecting mechanism comprising
       a pin-holding device composed of two parts forming a clamp whose two opposing faces have depressions extending in two intersecting planes, wherein the depressions in one plane are sized to enable pins 3–4 mm in diameter to be held in parallel with each other and the depressions in the second plane are sized to enable pins 5–6 mm in diameter to be held in parallel with each other;
       a collar for each pin-holding device that can releasably translate and rotate about the rigid support; and
       a removable screw for each pin-holding device,
    wherein the collar and the pin-holding device have crenellated surfaces made to contact one another to ensure precise indexing of the pin-holding device relative to the collar about a rotational axis of the collar, cohesion of the elements with each other, and full immobilization of the pins relative to the rigid support, and the removable screw provides omnidirectional locking of each connecting mechanism and each pin relative to the rigid support and its corresponding pin-holding device.

* * * * *

UNITED STATES PATENT AND TRADEMARK OFFICE
CERTIFICATE OF CORRECTION

| | | |
|---|---|---|
| PATENT NO. | : 6,652,523 B1 | Page 1 of 1 |
| APPLICATION NO. | : 09/582430 | |
| DATED | : November 25, 2003 | |
| INVENTOR(S) | : Evrard et al. | |

It is certified that error appears in the above-identified patent and that said Letters Patent is hereby corrected as shown below:

On the title page item (75) Inventors: please change "Michel Di Shino" to -- Michel Di Schino--.

On the title page item (73) Assignee: please change "Michel Di Shino" to -- Michel Di Schino--.

Signed and Sealed this

Twenty-seventh Day of March, 2007

JON W. DUDAS
*Director of the United States Patent and Trademark Office*